(12) United States Patent
Jia et al.

(10) Patent No.: US 6,787,629 B2
(45) Date of Patent: Sep. 7, 2004

(54) DENTAL RESIN MATERIALS, METHOD OF MANUFACTURE, AND USES THEREOF

(75) Inventors: Weitao Jia, Wallingford, CT (US); Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 73 days.

(21) Appl. No.: 10/287,428

(22) Filed: Nov. 4, 2002

(65) Prior Publication Data

US 2003/0125444 A1 Jul. 3, 2003

Related U.S. Application Data

(60) Provisional application No. 60/376,138, filed on Apr. 29, 2002, provisional application No. 60/359,252, filed on Feb. 20, 2002, and provisional application No. 60/336,883, filed on Nov. 2, 2001.

(51) Int. Cl.[7] .............................................. C08G 64/14
(52) U.S. Cl. ...................... 528/196; 528/106; 528/205; 523/115; 523/116; 523/117; 523/120; 524/537; 524/556; 524/494; 525/374
(58) Field of Search ................................ 528/196, 106, 528/205; 523/115, 116, 117, 120; 524/537, 556, 494; 525/374

(56) References Cited

U.S. PATENT DOCUMENTS

| | | | |
|---|---|---|---|
| 3,066,112 A | 11/1962 | Bowen | 260/41 |
| 3,179,623 A | 4/1965 | Bowen | 260/47 |
| 3,194,784 A | 7/1965 | Bowen | 260/41 |
| 3,751,399 A | 8/1973 | Lee et al. | 260/47 |
| 3,755,420 A | 8/1973 | Stoffey et al. | 260/486 R |
| 3,926,906 A | 12/1975 | Lee, II et al. | 260/42.53 |
| 4,306,913 A | 12/1981 | Mabie et al. | 106/288 B |
| 4,503,169 A | 3/1985 | Randklev | 523/117 |
| 4,544,359 A | 10/1985 | Waknine | 523/115 |
| 4,547,531 A | 10/1985 | Waknine | 523/116 |

(List continued on next page.)

Primary Examiner—David W. Wu
Assistant Examiner—Satya B Sastri
(74) Attorney, Agent, or Firm—Cantor Colburn LLP

(57) ABSTRACT

A dental resin composition is disclosed, comprising a polycarbonate-modified diphenoxy diacrylate having a monomer structure (I):

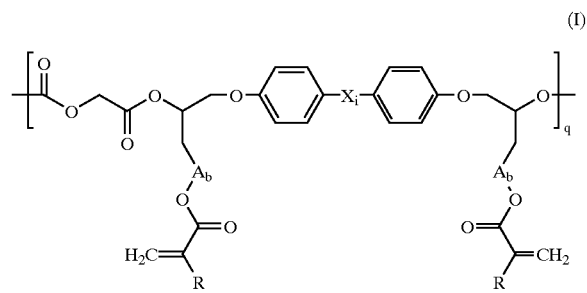

wherein R is $CH_3$ or H; b is one or zero; A is $(CH_2)_nO$; n is an integer from 1 to 10, preferably from 1 to 5; X is an alkoxy or cycloalkoxy group having from one to six carbon atoms, for example, 2,2-propylene or —$CH_2$—, or —S— or —O—; i is 1 or 0; and wherein M is —($C_{1\text{-}10}$ alkyl)O—, —$(CH_2)_pO$—, or —$CH(CH_3)CH_2O$—, m is an integer from 1 to 10, and p is an integer from 1 to 4. Preferably, R is methyl. The composition and described filler material are suitable for use in dental restorations, and provide improved wear resistance and other properties.

20 Claims, 1 Drawing Sheet

U.S. PATENT DOCUMENTS

| | | | |
|---|---|---|---|
| 4,764,497 A | 8/1988 | Yuasa et al. | 502/235 |
| 5,276,068 A * | 1/1994 | Waknine | 522/28 |
| 5,444,104 A * | 8/1995 | Waknine | 522/24 |
| 5,707,440 A | 1/1998 | Hengchang et al. | 106/485 |
| 5,726,068 A | 3/1998 | Rivin et al. | 436/167 |
| 5,861,445 A | 1/1999 | Xu et al. | 523/116 |
| 5,865,623 A | 2/1999 | Suh | 433/228.1 |
| 5,876,210 A | 3/1999 | Klee et al. | 433/226 |
| 5,936,006 A | 8/1999 | Rheinberger et al. | 523/116 |
| 5,969,000 A | 10/1999 | Yang et al. | 523/116 |
| 6,013,694 A * | 1/2000 | Jia et al. | 523/116 |
| 6,232,367 B1 | 5/2001 | Kobashigawa et al. | 523/116 |
| 6,270,562 B1 | 8/2001 | Jia | 106/35 |
| 6,362,251 B1 | 3/2002 | Alkemper et al. | 523/116 |
| 6,387,981 B1 | 5/2002 | Zhang et al. | 523/117 |
| 6,417,246 B1 | 7/2002 | Jia et al. | 523/113 |

* cited by examiner

DENTAL RESIN MATERIALS, METHOD OF MANUFACTURE, AND USES THEREOF

CROSS-REFERENCE TO RELATED APPLICATIONS

This application claims priority to U.S. application Ser. No. 60/336,883, filed Nov. 2, 2001, U.S. application Ser. No. 60/359,252, filed Feb. 20, 2002, and U.S. application Ser. No. 60/376,138, filed April 29, 2002, all of which are incorporated by reference herein in their entirety.

BACKGROUND OF THE INVENTION

This invention relates to novel resins and filler materials for restorative dentistry. Depending on resin and filler content, the resins and fillers may be used as crown and bridge materials, either with or without an alloy substrate; or as reconstructive materials, bioprostheses, restorative materials, filling materials, inlays, onlays, laminate veneers, dental adhesives and the like.

In recent years, materials used for dental restorations have comprised principally acrylate or methacrylate resins. Typical acrylate resinous materials are disclosed in U.S. Pat. No. 3,066,112 to Bowen, No. 3,179,623 to Bowen, No. 3,194,784 to Bowen, No. 3,751,399 to Lee et al. and No. 3,926,906 to Lee et al. An especially important methacrylate monomer is the addition product of bisphenol A and glycidyl methacrylate, 2,2'-bis [4-(3-methacryloxy-2-hydroxy propoxy)-phenyl]-propane (hereinafter abbreviated "Bis-GMA"). Polyurethane dimethacrylates (hereinafter abbreviated PUDMA) are also commonly used principal monomers in dental restorative materials. Since Bis-GMA is highly viscous at room temperature, it is generally diluted with an acrylate or methacrylate monomer having a lower viscosity such as trimethylolpropyl trimethacrylate, 1,6-hexanediol dimethacrylate, 1,3-butanediol dimethacrylate, and the like. Other dimethacrylate monomers, such as ethylene glycol dimethacrylate, diethylene glycol dimethacrylate, triethylene glycol dimethacrylate, and tetraethylene glycol dimethacrylate, are also in general use as diluents.

When these acrylic resinous materials were first developed, they were used for dental restorative purposes unfilled, that is, without the presence of any other organic or inorganic component. However, because acrylic materials exhibit high coefficients of thermal expansion relative to the coefficient of thermal expansion for the tooth structure, these unfilled substances proved to be less than satisfactory. The disparity in thermal expansion, coupled with high shrinkage upon polymerization, resulted in poor marginal adaptability and ultimately led to secondary decay. Furthermore, the wear and abrasion characteristics and the overall physical, mechanical, and optical properties of these unfilled acrylic resinous materials were quite poor. Composite dental restorative materials containing methacrylate resins and fillers were thus developed, the fillers generally comprising inorganic materials based on silica, silicate glass, or quartz. Particularly suitable improved inorganic filler materials include those disclosed in commonly assigned U.S. Pat. No. 4,547,531 to Waknine, and U.S. Pat. No. 4,544,359 to Waknine.

There are now available resins that exhibit high diametral tensile strength, excellent optical properties and polishability, and low water sorption while at the same time complying with all of the requirements specified in ADA Specification No. 27 for Direct Filling Resins. Exemplary materials comprise monomers and polymers disclosed in commonly assigned U.S. Pat. No. 5,276,068 to Waknine and U.S. Pat. No. 5,444,104 to Waknine. Such materials make use of a novel polycarbonate dimethacrylate (PCDMA) which is the condensation product of two parts of hydroxy-alkylmethacrylate of the formula $H_2C=C(CH_3)C(O)O-A-OH$, in which A is a $C_1-C_6$ alkylene, and 1 part of a bis(chloroformate) of the formula $ClC(O)-(OR)_n-OC(O)Cl$, in which R is a $C_2-C_5$ alkylene having at least two carbon atoms in its principal chain, and n is an integer from 1 to 4. This polycarbonate dimethacrylate imparts excellent strength to the cured resin, but it is somewhat costly. Another advantageous resin having lower water sorption characteristics, as disclosed in U.S. Pat. No. 5,969,000, is an ethoxylated bisphenol A dimethacrylate (EBPDMA) having the structure $CH_2=C(CH_3)CO_2(C_2H_4)_xC_6H_4C(CH_3)_2C_6H_4(C_2H_4)_yO_2CC(CH_3)=CH_2$, wherein x+y is an integer from 1 to 20, and preferably from 2 to 7. While such resins are well suited for their intended purposes, there is a perceived need in the art for dental resin materials with even more advantageous physical properties, particularly strength, water sorption, and wear.

Current dental restorative composites are continuously being developed to improve strength, wear resistance, and other chemical and physical working and handling properties. One of the main challenges associated with achieving an optimal composite is the development of improved filler compositions. Numerous attempts have been made in recent decades to create optimal fillers suitable for dental composites. These efforts have included reducing the size of glass/ceramic fillers, creating sol-gel spherical microparticles, surface modification of particles/fibers, and treatment of amorphous silica particles. Although some of these efforts have provided some improved properties of dental composites, there remains a continuing need for improved, highly functional filler material.

SUMMARY OF THE INVENTION

The above-described drawbacks and disadvantages are alleviated by a dental resin composition comprising a curable polycarbonate-modified diphenoxy diacrylate having the structure (I):

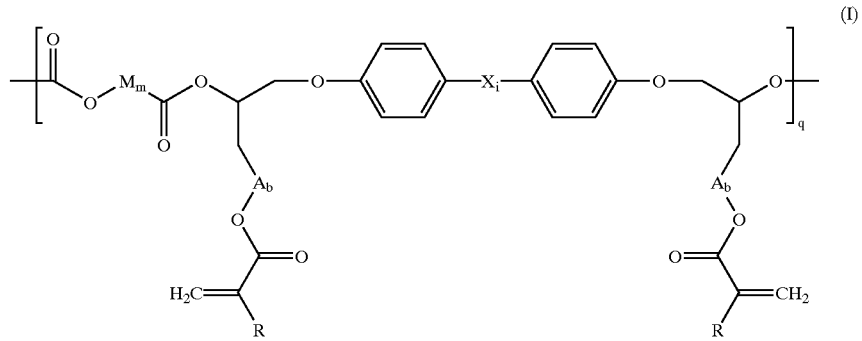

wherein R is $CH_3$ or H; b is one or zero; A is $O(CH_2)_n$; n is an integer from 1 to 10; X is an alkyl or cycloalkyl group having from one to six carbons, S, or O; i is 1 or 0; M is an alkoxy or cycloalkoxy group having from one to ten carbon atoms, preferably $(CH_2)_pO$ wherein p is an integer from one to four or $CH(CH_3)CH_2O$; m is an integer from one to ten; and q is an integer from 1 to about 100.

In one embodiment, there is provided filled dental resin restorative compositions comprising the above-described diphenoxy diacrylate, optional ethylenically unsaturated comonomers and oligomers, optional diluent monomers to increase the surface wettability of the resinous matrix, and various inorganic additives and/or fillers and filler materials. Such filled compositions are useful for a variety of dental treatments and restorative functions including crown and bridge materials, dental adhesives, luting agents, cements, denture-base materials, orthodontic material, sealants, and other dental restorative materials.

In another embodiment, there is provided filled dental resin restorative compositions comprising the above-described diphenoxy diacrylate, optional ethylenically unsaturated comonomers and oligomers, optional diluent monomers to increase the surface wettability of the resinous matrix, and a silica sol derived filler material.

In still another embodiment, an improved filler material for dental compositions comprising particles derived from a silica sol, wherein the silica sol comprises nanometer sized particulates, and wherein the filler material comprises at least one crystalline phase, preferably a mixture of crystalline and amorphous phases, is disclosed. A further filler material is disclosed derived from a composition comprising a silica sol, a glass filler, a ceramic filler, or a mixture thereof, wherein the silica sol comprises nanometer sized particulates, and the filler comprises at least one crystalline phase, preferably a mixture of crystalline and amorphous phases, and the glass filler, ceramic filler, or mixture thereof comprise microparticulate sizes. Methods of making the silica sol filler material are described.

BRIEF DESCRIPTION OF THE DRAWING

The FIGURE is an x-ray diffraction pattern showing three different samples of filler materials.

DETAILED DESCRIPTION

Figure 1:
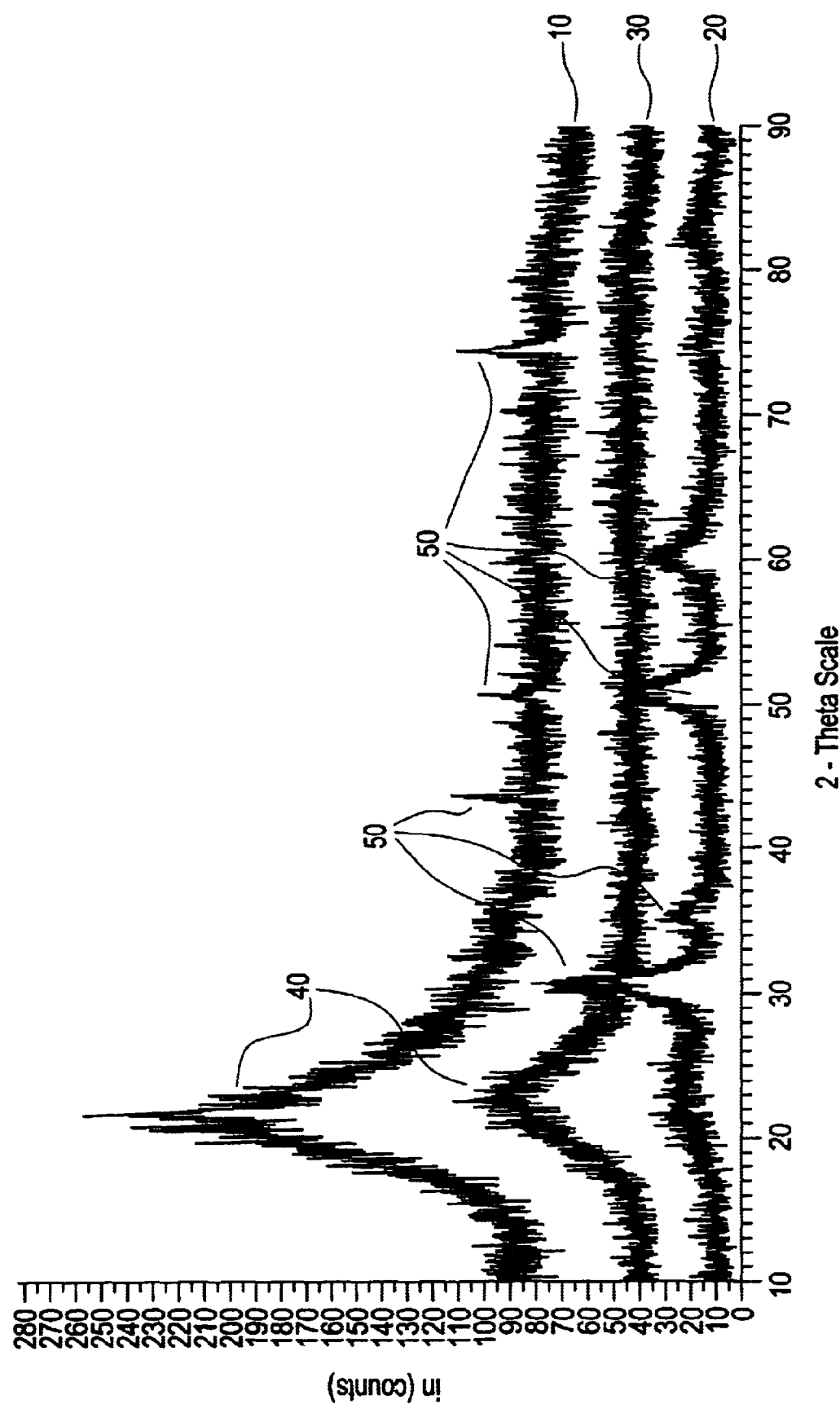

A dental restorative composition with improved properties comprises a curable polycarbonate-modified diphenoxy diacrylate having the structure (I):

wherein R is $CH_3$ or H; b is one or zero; A is $O(CH_2)_n$; n is an integer from 1 to 10; X is an alkyl or cycloalkyl group having from one to six carbons, S, or O; i is 1 or 0; M is an alkoxy or cycloalkoxy group having from one ten carbon atoms, preferably $(CH_2)_pO$ wherein p is an integer from one to four or $CH(CH_3)CH_2O$; m is an integer from one to ten; and q is an integer of 1 or greater, preferably 5 or greater, and more preferably about 10 or greater. Also, q is preferably an integer less than about 100, more preferably less than about 75, and most preferably less than about 50. As used herein "diacrylate" is intended to encompass both the acrylate (R=H) and methacrylate (R=$CH_3$) functionalities. When cured, this resin material has excellent strength, water sorption, and other properties, particularly improved wear properties.

Preferably, b is zero; and when b is one, A is preferably $CH_2CH_2O$ or $CH_2CH_2CH_2O$.

One preferred diphenoxy diacrylate has the structure (I) wherein R is methyl, b is zero, X is 2,2-propylene, i is 1, M is $CH_2CH_2O$ and m is 2.

Another preferred diphenoxy diacrylate has the structure (I) wherein R is methyl, b is zero, X is 2,2-propylene, i is 1, M is $CH_2CH_2O$ and m is 3.

Another preferred embodiment has the structure (I) wherein R is methyl, b is zero, X is $CH_2$, i is 1, M is $CH_2CH_2O$ and m is 2.

Another preferred embodiment has the structure (I) wherein R is methyl, b is zero, X is $CH_2$, i is 1, M is $CH_2CH_2O$ and m is 3.

Still another preferred diphenoxy diacrylate has the structure (I) wherein R is methyl, A is $CH_2CH_2O$, b is 1, X is $CH_2$, i is 1, M is $CH_2CH_2O$ and m is 2.

Yet another preferred diphenoxy diacrylate has the structure (I) wherein R is methyl, A is $CH_2CH_2O$, b is 1, X is $CH_2$, i is 1, M is $CH_2CH_2O$ and m is 3.

Polycarbonate-modified diphenoxy diacrylates (I) may be obtained by the reaction of a diphenyl glycidyl ether having the general formula (II):

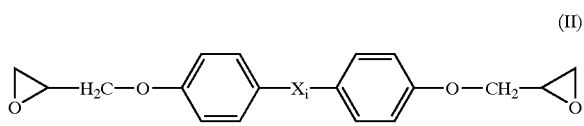

(II)

wherein X is as described above and i is 1 or 0, with an acrylate of the general formula (III):

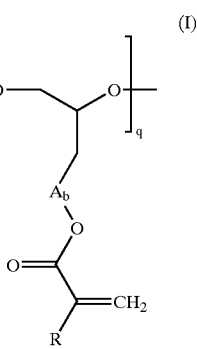

(I)

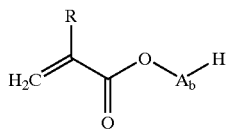

(III)

wherein b is 1 or 0; A is as described above; n is an integer in the range from 1 to 10, preferably in the range from 1 to 5; and R is $CH_3$ or H, to form the diphenoxy diacrylate. This diphenoxy diacrylate is further reacted through the hydroxy group (or a chemical equivalent of the hydroxy group) with a bis(haloformate), preferably a bis(chloroformate) having the structure $ClC(O)OM_mC(O)Cl$, or a chemical equivalent thereof, wherein m and M are as described above, to yield the polycarbonate diphenoxy diacrylate (I).

Use of the polycarbonate-modified diphenoxy diacrylates (I) results in cured (polymerized) dental compositions having improved physical properties, including hardness, double bond conversion percentage, and depth of cure. When used to form dental compositions, polycarbonate diphenoxy diacrylates (I) may be used as the only resinous component, or in combination with other ethylenically unsaturated resinous monomer and/or oligomer components which will co-polymerize with (I). Acrylate and methacrylate monomers and oligomers for use as the ethylenically unsaturated resin component are known in the art, and may include the viscous acrylate or methacrylate monomers such as those disclosed in U.S. Pat. No. 3,066,112 to Bowen, No. 3,179,623 to Bowen, No. 3,194,784 to Bowen, No. 3,751, 399 to Lee et al., No. 3,926,906 to Lee et al., and commonly assigned U.S. Pat. No. 5,276,068 and No. 5,444,104 to Waknine, all of which are incorporated herein by reference. Other acrylate- or methacrylate-containing monomers or oligomers include, but are not limited to, polyurethane dimethacrylate (PUDMA), diurethane dimethacrylate (DUDMA), and other monomers and oligomers known in the art. A useful oligomer is disclosed in U.S. Pat. Nos. 5,276,068 and 5,444,104 to Waknine, being a polycarbonate dimethacrylate (PCDMA) which is the condensation product of two parts of a hydroxyalkylmethacrylate and one part of a bis(chloroformate). Another advantageous resin for use in the curable resin component and having lower water sorption characteristics is an ethoxylated bisphenol A dimethacrylate (EBPDMA) as disclosed in U.S. Pat. No. 6,013,694. The foregoing monomers and oligomers are also termed viscous polymerizable components. Included within the scope of the resin compositions herein are the resin compositions suitable for use with glass ionomer cements, including polycarboxylic acids such as homo-and copolymers of acrylic acid and/or itaconic acid.

In addition to the aforementioned viscous polymerizable components (ethylenically unsaturated resinous monomer and/or oligomer components), the resinous dental compositions can further include a diluent monomer to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; and diol dimethacrylates such as butanedimethacrylate, dodecanedimethacrylate, or 1,6-hexanedioldimethacrylate (HDDMA). Tri(ethylene glycol) dimethacrylate (TEGDMA) and HDDMA is particularly preferred.

When used to form dental compositions, polycarbonate diphenoxy diacrylates (I) are generally present in an amount less than or equal to about 80 percent by weight, with less than or equal to about 70 percent by weight preferred, and less than or equal to about 60 percent by weight of the total resin composition more preferred. Also preferred is an amount greater than or equal to about 10 weight percent, with greater than or equal to about 20 weight percent preferred, and greater than or equal to about 30 weight percent of the total resin composition more preferred.

Other ethylenically unsaturated monomers or oligomers, preferably urethane dimethacrylate (UDMA), PCDMA, Bis-GMA, and/or EBPDMA, are incorporated into the resinous composition in an amount of about 20 to about 90 weight percent of the total resin composition. When no diluent monomer is used, the preferred range for polycarbonate diphenoxy dimethacrylates (I) is about 40 to about 90 weight percent, and most preferably about 60 weight percent of the total resin composition, and the preferred range for the other ethylenically unsaturated monomers or oligomers is about 1 to about 70 weight percent, and most preferably about 40 weight percent of the total resin composition. The diluent monomers, when present, are typically used in an amount from about 0 to about 40 weight percent of the total resin composition.

In addition to the above monomers and oligomers, the resinous dental compositions also typically include polymerization initiators, polymerization accelerators, ultraviolet light absorbers, anti-oxidants, and other additives well known in the art.

Suitable polymerization initiators are those conventional initiators known in the art. For example, visible light curable compositions employ light-sensitive compounds such as benzil diketones, and in particular, DL-camphorquinone (CQ) in amounts ranging from about 0.05 to about 0.5 weight percent. Self-curing compositions will generally contain free radical polymerization initiators such as, for example, a peroxide in amounts ranging from about 2 to about 6 weight percent. Particularly suitable free radical initiators are lauryl peroxide, tributyl hydroperoxide and, more particularly benzoyl peroxide.

Polymerization accelerators suitable for use are the various organic tertiary amines well known in the art. In visible light curable compositions, the tertiary amines are generally acrylate derivatives such as dimethylaminoethyl methacrylate and, particularly, diethylaminoethyl methacrylate ("DEAEMA"), and the like, in an amount of about 0.05 to about 0.5 wt %. In the self-curing compositions, the tertiary amines are generally aromatic tertiary amines, preferably tertiary aromatic amines such as ethyl 4-(dimethylamino) benzoate (commonly known as "EDMAB"), 2-[4-(dimethylamino)phenyl] ethanol, N, N-dimethyl-p-toluidine (commonly abbreviated "DMPT"), bis(hydroxyethyl)-p-toluidine, triethanolamine, and the like. Such accelerators are generally present at about 0.5 to about 4.0 wt % in the polymeric component.

It is furthermore preferred to employ an ultraviolet absorber in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV-5411 available from American Cyanamid Company.

The dental compositions may be unfilled, filled, or partially filled. The filled compositions can include many of the inorganic fillers currently used in dental restorative materials, the amount of such filler being determined by the specific function of the filled materials. Thus, for example, where crown and bridge materials are being prepared, the resinous composition is are present in amounts of about 10 to about 40 weight percent of the total composition, and the filler materials are present in amounts of about 60 to about 90 weight percent of the total composition. Typical compositions for crown and bridge materials are about 25 percent by weight of the resinous material and about 75 percent by weight of the filler.

Suitable fillers are known in the art, and include those that are capable of being covalently bonded to the resin matrix itself or to a coupling agent that is covalently bonded to both. Examples of suitable filling materials include but are not limited to, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Particularly suitable fillers are those having a particle size in the range from about 0.1 to about 5.0 micrometers, mixed with a silicate colloid of about 0.001 to about 0.07 micrometers. Some of the aforementioned inorganic filling materials and methods of preparation thereof are disclosed in U.S. Pat. No. 4,544,359 and No. 4,547,531, pertinent portions of which are incorporated herein by reference.

A preferred filler is derived from a silica sol as described herein, and comprises at least one of crystalline phase. In a preferred embodiment, the filler material disclosed herein is for use in dental composites to produce high strength, high functioning dental materials. The filler is produced by a unique process that involves the steps of drying, heating, and preferably silanizing an aqueous or organic sol of silica particles to form a filler material referred to hereinafter as the "sol derived filler". The aqueous sol contains about 15 to about 30 percent of amorphous, elongated, bound silica particles in an aqueous solution. The silica particle diameters can be less than or equal to about 50 nanometers, with less than or equal to about 30 nanometers preferred, and less than or equal to about 20 nanometers more preferred. Also preferred is a silica particle diameter of greater than or equal to about 1 nanometer, with greater than or equal to about 5 nanometers more preferred, and greater than or equal to about 10 nanometers especially preferred (all particles in the nanometer ranges being referred to as nano-particulates). The particles may be bound to each other so as to result in chains having lengths of less than or equal to about 400 nanometers, with less than or equal to about 300 nanometers preferred, and less than or equal about 200 nanometers more preferred. Also preferred are chain lengths of greater than or equal to about 10 nanometers, with greater than or equal to about 20 nanometers more preferred, and greater than or equal to about 40 nanometers especially preferred. Such silica is commercially available as a colloidal silica sol in water form Nissan Chemical Industries, Ltd, under the trade names SNOWTEX-PS-S™, SNOWTEX-PS-M™, SNOWTEX-PS-L™, and MA-ST-UP™, all from Nissan Chemical Company. Without being bound by theory, it is hypothesized that the "strings" or "pearls" of bound silica improve fracture resistance compared to discrete, particulate materials. U.S. Pat. No. 6,417,246 discloses suitable filler compositions and is hereby incorporated by reference.

The (aqueous or organic) sol of silica is initially dried at a temperature to remove the liquid (e.g., water, methanol, or the like) present. The temperature range for drying may be from about 30 to about 200° C. Thereafter, the dried powder is heated at about or above about 600° C. Preferably, the powder is heated at about or above about 800° C. to produce a silica filler having a least one crystalline phase, and preferably a mixture of crystalline and amorphous phases. Heat treatment of the powder produced from the aqueous or organic sol produces a filler having increased strength, due to the formation of the crystalline phase(s). An x-ray diffractometer is used to determine the formation or presence of crystal phases present. Without being bound by theory, the particles retain nanostructured character.

In order to improve bonding of the filler with a resin matrix, the heat-treated silica particles are preferably treated with a silane, for example gamma-mercaptopropyltrimethoxysilane, gamma-mercaptopropyltriethoxysilane, gamma-aminopropyltriethoxysilane, and the like. The material is then ready for mixture with a resin material for manufacture of a dental composite.

In yet another embodiment, an aqueous or organic silica sol, as described above, is mixed with one or more other particulate filler materials during the treatment process to form what is referred to hereinafter as "a hybrid filler", preferably comprising some particles that are nanosized and microsized. Preferably a mixture of the (untreated) nano-particulate silica sol is combined with a micro-particulate filler. Other conventional additives may also be included in the mixture, such as, but not limited to radiopaquing or opacifying agents. The micro-particulate filler contains particles having sizes less than or equal to about 5 micrometers, with less than or equal to about 4 micrometers preferred, and less than or equal to about 1 micrometer more preferred. Also preferred is a particle having sizes greater than or equal to about 0.1 micrometer, with greater than or equal to about 0.2 micrometer more preferred, and greater than or equal to about 0.6 micrometer especially preferred (all particles in the micrometer ranges being referred to as micro-particulates). Examples of suitable micro-particulate glass or ceramic filling materials include, but are not limited to, silica, silicate glass, quartz, barium oxide, barium silicate, strontium silicate, barium borosilicate, strontium borosilicate, borosilicate, lithium silicate, lithium alumina silicate, zinc oxide, calcium oxide, tantalum dioxide, amorphous silica, ammoniated or deammoniated calcium phosphate and alumina, zirconia, tin oxide and titania. Examples of commercially available ground dental glass fillers having particles sizes in the range of about 0.5 to about 2 micrometers are sold under the trade names 8235™, GM27884™, and in other particles sizes are sold under the trade names FK 0.4™, FK 0.7™, FK 1.0™, FK 1.5™ etc., all from Schott Glas. The mixture may further comprise unbound silicate colloids of about 0.001 to about 0.07 micrometers.

The process of producing a hybrid filler of nano- and micro-particulate fillers includes preparing an aqueous or organic solution of a micro-particulate glass or ceramic filler under acidic or neutral conditions (up to about a pH of 7) and preferably under acidic conditions or with a pH of from about 1 to about 4. The micro-particulate filler is dispersed into the solution by means of stirring, sonification or other proper means or their combinations. Next, an aqueous or organic silica sol is gradually added into the above solution while stirring to form a gel. The gel is then dried, preferably in shallow pans or in thin films, with a conventional gravity-drying oven for a slow drying or furnace for quick drying at a temperature to remove the liquid present. The temperature range for drying may be from about 30 to about 200° C. The dried powders are then collected and pulverized. The powder is next fired at a temperature and time sufficient to fuse the nano-particulate pearl-like silica onto the microparticulate glass or ceramic surfaces. The dried powder may be heated at about or above about 600° C. and preferably, the powder is heated at about or above about 800° C. to fuse the nano-particulate pearl-like silica onto the micro-particulate glass or ceramic surfaces. The fired particles are further subject to pulverization or milling to break the agglomerates and surface silane treatment to improve bonding of the filler with a resin matrix. Examples of silanes useful herein include, but are not limited to, gamma-mercaptopropyltrimethoxysilane, gamma-mercaptopropyltriethoxysilane, gamma-aminopropyltriethoxysilane, and the like.

In these hybrid fillers, the portion of material derived from the sol is present in an amount of less than or equal to about 90 percent by weight based on the total weight of the filler, with less than or equal to about 80 percent by weight preferred, and less than or equal to about 70 percent by weight more preferred. Also preferred is the portion of material derived from the sol present in an amount of greater than or equal to about 40 percent by weight, with greater than or equal to about 50 percent by weight more preferred, and greater than or equal to about 60 percent by weight based on the total weight of the filler especially preferred. The micro-particulate filler is present in an amount of less than or equal to about 20 percent by weight, with less than or equal to about 10 percent by weight preferred, and less than or equal to about 5 percent by weight more preferred. Also preferred is the micro-particulate filler present in an amount of greater than or equal to 0 percent by weight, with greater than or equal to about 1 percent by weight more preferred, and greater than or equal to about 2 percent by weight especially preferred.

In yet another embodiment herein, another hybrid filler is derived from an aqueous or organic solution of an opacifying metal oxide or calcinable precursor compound including, but not limited to, zirconia, zirconium acetate, bismuth acetate, bismuth oxychloride, or the like. This hybrid filler is prepared under acidic or neutral conditions (up to about a pH of 7) and preferably under acidic conditions or with a pH of from about 1 to about 4. A micro-particulate filler material is then dispersed into the solution by means of stirring, sonification or other proper means or their combinations. Thereafter, an aqueous or organic silica sol is gradually added into the above solution while stirring to form a gel. The gel is then dried, preferably in shallow pans or in thin films, with a conventional gravity drying oven for a slow drying or furnace for quick drying. The dried powders are then collected and pulverized. The powder is next fired at a temperature and time sufficient to fuse the nano-particulate, pearl-like silica onto the micro-particulate glass or ceramic surfaces. The dried powder may be heated at about or above about 600° C. and preferably, the powder is heated at about or above about 800° C. to fuse the nano-particulate pearl-like silica onto the micro-particulate glass or ceramic surfaces. The fired particles are further subject to pulverization or milling to break the agglomerates and to surface silane treatment.

In these hybrid fillers, the portion of material derived from the sol is present in an amount of less than or equal to about 90 percent by weight based on the total weight of the filler, with less than or equal to about 80 percent by weight preferred, and less than or equal to about 70 percent by weight more preferred. Also preferred is the portion of material derived from the sol present in an amount of greater than or equal to about 40 percent by weight, with greater than or equal to about 50 percent by weight more preferred, and greater than or equal to about 60 percent by weight based on the total weight of the filler especially preferred. The portion of the material derived from the opacifying metal oxide or calcinable precursor is present in an amount of less than or equal to about 20 percent by weight, with less than or equal to about 10 percent by weight preferred, and less than or equal to about 5 percent by weight more preferred. Also preferred is the portion of the material derived from the opacifying metal oxide or calcinable precursor compound present in an amount of greater than or equal to 0 percent by weight, with greater than or equal to about 1 percent by weight more preferred, and greater than or equal to about 2 percent by weight especially preferred.

As with conventional fillers, the amount of total filler comprising one or more of the above-described sol derived filler or hybrid fillers in the dental composite can vary widely, being in the range from about 1 to about 90 percent by weight of the total composition. The amount used is determined by the requirements for the particular application. Thus, for example, crown and bridge materials generally comprise form about 60 to about 90 weight percent filler; luting cements comprise from about 20 to about 80 weight percent filler; sealants generally comprise form about 1 to about 20 weight percent filler; adhesives generally comprise from about 1 to about 30 weight percent filler; and restorative materials comprise from about 50 to about 90 weight percent filler, with the remainder in all cases being the resin composition.

The sol derived filler may be used in combination with other suitable fillers known in the art of dental compositions to create what is referred to hereinafter as a "sol derived mixed filler". The final finished hybrid fillers can also be used in combination with other suitable fillers known in the art of dental composites to create restorative materials with improved strength, and esthetic and desirable working characteristics. The hybrid filler in combination with other suitable fillers are referred to hereinafter as "hybrid-mixed fillers". In these mixed fillers, the amount of the sol derived filler and/or mixed filler relative to other filler may also vary widely, depending on the requirements of the particular application. The sol derived filler and/or hybrid filler may accordingly comprise up to about 100 weight percent of the total filler composition, preferably from about 1 to about 90 weight percent for sealers and adhesives, and from about 2 to about 90 weight percent for crown and bridge materials and dental restorative materials. Other additives, such as opacifying agents may be present in an amount of less than or equal to about 50 percent by weight, with less than or equal to about 40 percent by weight preferred, and less than or equal to about 30 percent by weight more preferred. Also preferred is the additive present in an amount of greater than or equal to 0 percent by weight, with greater than or equal to about 10 percent by weight more preferred, and greater than or equal to about 20 percent by weight especially preferred.

The above described filler materials may be combined with a variety of composite forming materials to produce high strength along with other beneficial physical and chemical properties. Preferably, the filler is mixed with a resinous material to form high-strength dental composites. Suitable resin materials include those mentioned herein. A preferred resin comprises a polycarbonate-modified diphenoxy diacrylate (I), described herein.

The more viscous monomers, i.e. UDMA, Bis-GMA, and the like are generally present in an amount of less than or equal to about 100 percent by weight, with less than or equal to about 90 percent by weight preferred, and less than or equal to about 80 percent by weight based on the total weight of the composition more preferred. Also preferred is the viscous monomer present in an amount of greater than or equal to about 30 percent by weight, with greater than or equal to about 50 percent by weight of the total resin composition more preferred. Diluent monomers, when present, are incorporated into the resin composition in an amount from about 1 to about 70 weight percent of the total resin composition.

U.S. Pat. Nos. 4,503,169, 4,764,497, 5,707,440, 5,861,445, 6,013,694, 6,232,367, and 6,270,562 disclose various filler materials and dental composites and are hereby incorporated by reference.

Methods for use of the above-described compositions are well known in the art. For example, a site to be restored in a tooth is prepared, and the above-described composition is applied to the site. The invention is further is illustrated by the following non-limiting examples.

EXAMPLES

Example 1

Synthesis of Bis[p-(3-ethoxymethacryloxy-2-hydroxy propoxy)-phenyl]-methane (BEPDMA)

Bis(4-glycidyloxyphenyl)methane (170 g, 0.5 mol) and 2-hydroxyethyl methacrylate (136 g, 1.05 mol) were mixed with magnetic stirring at room temperature. One mol percent to 8 mol percent of catalyst (tin (II) 2-ethylhexanoate) was added dropwise to the above mixture. The mixture was heated to 100° C.–150° C. for 4–10 hours. The reaction was monitored by Fourier Transform Infrared (FTIR) until the end epoxy group disappeared. The yield was 100 percent.

Example 2

Synthesis of Bis[p-(3-methacryloxy-2-hydroxy propoxy)-phenyl]-methane (BPDMA)

Methacrylic acid (95 g, 1.1 mol) was mixed with 0.5 weight percent to 5 weight percent of catalyst [N,N-dimethyl-p-toluidine, (DMPT)] at room temperature. Bis (4-glycidyloxphenyl)methane (170 g, 0.5 mol) was added into the above mixture. The mixture was heated to 50° C.–70° C. for 4–10 hours. The reaction was monitored by FTIR spectrometer until the end epoxy group disappeared. The yield was 100 percent.

Example 3

Synthesis of Polycarbonate Modified-BisGMA (PCBisGMA), -BEPDMA (PCBEPDMA) and -BPDMA (PCBPDMA)

BisGMA (51 G, 0.1 mol), (47.0 g, 0.1 mol) or BPDMA (42.6 g, 0.1 mol) was dissolved in 200 ml of ethyl acetate. Triethylamine (14.5 ml, 0.12 mol) was added into the solution. Then triethylene glycol bischloroformate (10.25–20.5 ml, 0.05–0.1 mol) was added dropwise into the mixture. The reaction was stirred for 1–5 hours. The solution was washed successively with 1M HCl solution, 1M NaOH solution, and saturated NaOH solution. The organic phase was finally dried over anhydrous $MgSO_4$. The resin was collected after evaporating the solvent by rotary evaporator.

Example 4

Various physical properties of PCBis-GMA and Bis-GMA were tested and are shown in Table 1. Weight average molecular weight was tested by gel permeation chromatography (GPC) using polystyrene as the standard. Water absorption was tested in accordance with ISO 4049. Shrinkage was tested by a mercury dilatometer. Double bond conversion was measured by FT-IR spectrometer.

TABLE 1

| Resin | Molecular Weight | Refractive Index | Water Absorption (microgram/ $mm^3$/week) | Shrinkage (percent) | Double Bond Conversion (percent) |
|---|---|---|---|---|---|
| Bis-GMA | 500 | 1.5557 | 35 | 4.44 | 40 |
| PCBis-GMA | 2,000 | 1.5315 | 20 | 3.49 | 36 |

Example 5

Various physical properties of PCBisGMA in combination with other another resin and diluent (EBPDMA and TEGDMA) in a weight ratio of 30/60/10 (Resin 1) were tested. As a comparison, PCDMA in combination with EBPDMA in a weight ratio of 30/70 (Resin 2) was also tested. Each composition further comprised 0.2 wt. %t CQ and 0.2 wt. % DEAEMA, and were light cured. Table 2 shows the test results of the two resin systems.

TABLE 2

| Resin | Flexural strength (psi) | Water absorption (microgram/$mm^3$/week) | Weight loss (g/$mm^3$/week) |
|---|---|---|---|
| Resin 1 | 16445 (810) | 11 | 3.4 |
| Resin 2* | 13837 (2138) | 10 | 4.2 |

*Comparative Example

Example 6

The mechanical properties and curing abilities of pastes using Resin 1 of Example 5 are listed in Table 3. A flowable paste (Paste 1) was prepared using 35 wt. % Resin 1 and 65 wt. % silane treated barium borosilicate glass. Another highly filled paste (Paste 2) was made using 27 wt. % Resin 1, 12 wt. % fumed silica, and 61 wt. % silane treated barium borosilicate glass.

Barcol hardness was measured with a Barcol hardness impressor after top curing for 10 seconds under visible light in a 3 mm mold. Depth of cure (mm) was measured using a 5 mm mold after 10 seconds of top curing with a visible light.

TABLE 3

| Sample | Paste 1 | Paste 2 |
|---|---|---|
| Flexural Strength (psi) | 19844 (1025) | 18700 (2086) |
| Depth of cure (mm) | 4.318 | 5.0 |
| Barcol hardness (top/bottom) | 80/65 | 82/72 |

Example 7

In vitro Wear Resistance Test

To compare the in vitro wear resistance of a PCBisGMA composite to commercially available samples, a wear device designed by the University of Alabama School of Dentistry (UAB) was used. Wear was tested according to generalized (surface wear) and localized wear. A PCBisGMA composite (Table 4) and two commercially available composites, Esthet-X® (Dentsply/Caulk) and Z250 (3M), were tested in the wear device according to the following procedure

TABLE 4

| Components | Wt. percent |
|---|---|
| PCBisGMA | 5.10 |
| BisGMA | 7.45 |
| UDMA | 5.72 |
| HDDMA | 5.61 |
| BHT | 0.005 |
| UV-5411 | 0.20 |
| Camphorquinone | 0.05 |
| EDMAB | 0.11 |
| Lucirin TPO | 0.05 |
| UVITEX-OB | 0.005 |
| Barium zirconium silicate* | 32.0 |
| Barium borosilicate | 36.0 |
| Silica | 4.6 |
| Methacryloxysilane | 3.0 |
| FD&C pigments: Y #5, Red #40 and Iron oxide black | <0.1 |

*The barium zirconate silicate is a nanohybrid filler made in accordance with Example 8 below (Powder 2).

To test for generalized wear, sound, caries-free extracted human molars were selected for mounting in a brass specimen holder. The occlusal surface was ground flat using a series of metallographic papers. Care was taken so that the ground surface consisted of enamel. After surfacing, a well-defined cylindrically shaped cavity preparation was developed in the center of the tooth specimen. The geometry of the preparation was approximately 4.0 mm in diameter and 3.0 mm in depth. All of the cavosurface margins were carefully finished with a sharp carbide bur (No. 245/225).

The prepared cavity was restored with the above PCBisGMA formulation or one of the two commercial materials. Bond-3 (Pentron Corp.) was used for the PCBisGMA composite restoration, Prime&Bond® (Dentsply/Caulk) NT was used for Esthet-X®, and Single Bond (3M) was used for the Z250 restoration. The bonding and restorations were carried out according to the manufacturer's instructions. The restored surface was then ground flat using a series of silicone carbide papers. The final surface was finished with 600 grit and polished with alumina/water slurry. All of this was done using a special hand held device to ensure the flat occlusal surface was parallel to a horizontal plane and parallel to the flat surface of the energy-generating stylus.

Using a specially designed aligning device, the mounted specimen was inserted into the wear testing apparatus. The mounted tooth was then surrounded by a tight fitting cylinder or ring that was filled with a water slurry of unplasticized polymethylmethacrylate beads (average diameter=44 micrometers). This assembly, along with a bank of three other specimens, were submerged into a room temperature water bath.

At this point, a flat-planed stylus machined from DELRIN® brand polyacetal, was positioned over the restored area. The diameter of the flat stylus was approximately 8 mm and was appropriately centered so that it completely covered the entire restoration. At a rate of 1.2 times per second, the stylus was vertically loaded onto the restored surface under a load of 17 pounds or 75.6 Newton. As soon as the stylus contacted the specimen, it automatically rotated clockwise 15 degrees. Then after counter-rotating, the stylus moved upward vertically to its original position. The entire cycling procedure was carried out 400,000 times, which took approximately 90 hours of continuous running. The masticatory load was applied to the specimen surface through the slurry of PMMA beads.

Upon completion of the wear test, two replicas of the surface were prepared with the REPROSIL® (Caulk). These were converted into epoxy die model material. The first was used for microstructural evaluation using scanning electron microscopy. The second was used for wear determinations using a profilometer. In essence, the profilometer traversed across the specimen surface in a single plane each 45 degrees thereby producing eight different readings for wear.

Loss of resin composite along the wall of the cavity preparation was measured and converted into micrometers. The data were then analyzed statistically. Comparisons among materials were done by a one-way analysis of variance (ANOVA).

Localized wear was determined similarly, except that rather than employing a flat stylus for imparting a load to the occlusal surface, a blunted conical stylus made of hardened steel was used. Again, after the stylus contacted the surface, it rotated 15 degrees. After achieving maximum loading, the stylus counter rotated and moved vertically to its original position, such that rather than developing a generalized pattern of wear, the wear was localized. The numbers of cycles was only 100,000 as compared to the 400,000 cycles using to develop a generalized wear pattern. Replicas were generated of each surface and poured with the Epoxy Die. Using scanning electron microscopy, images were generated of the defect at 50 and 500 magnification. Profilometric tracings were made through the localized wear defect. Wear depth of localized wear area were calculated in micrometers.

The results of the generalized and localized wear are shown in Table 5. The mean values of wear depth are in micrometers. Based upon the results of these in vitro tests, it is possible to predict the long-term clinical performance of the composite resin under investigation. It is also possible to rank the wear resistance of the material to a series of other proprietary materials tested under the same condition as well as clinically.

TABLE 5

| | Generalized Wear | | |
|---|---|---|---|
| Materials | Surface | Marginal | Localized wear |
| PCBisGMA Composition | 3.8 ± 1.0 | 11.2 ± 3.5 | 47.4 ± 16.1 |
| Z250 | 9.8 ± 0.6 | 17.6 ± 3.4 | 52.9 ± 19.3 |
| Esthet-X ® | 13.1 ± 5.8 | 13.1 ± 3.6 | 49.8 ± 13.4 |

The results of the generalized wear (surface wear) for PCBisGMA composite exhibited the least amount of wear, followed by Z250, and Esthet-X®. The wear value after 400,000 cycles of generalized wear test well correlates to the three-year clinical wear value. It is estimated that the annual wear rate of PCBisGMA will be approximately 1.3 micrometers. The results of marginal wear represent the wear of bonding agent.

Example 8

Formation of Silica Sol Derived Filler Materials, Powder 1

A control powder was formed by drying about 500 grams of Nissan Snowtex PS-M™ colloidal silica sol (which contains about 20 percent of the elongated, bound silica particles having diameters of 10 to 20 nanometers and lengths of 40 to 200 nanometers) in a glass tray and heating at about 70° C., until dry. The powders (about 100 grams) were collected and pulverized with a mortar and pestle and subjected to X-ray diffraction. As shown in FIG. 1, the control sample (30) showed a dominant amorphous curve (40). No crystalline peaks are present.

Powder 1 was prepared as above, except that after being pulverized, the powders were placed into an $Al_2O_3$ crucible and fired at about 800° C. for about one hour. An X-ray diffraction measurement was performed on the powder sample to determine the crystalline formation in the sample. As shown in FIG. 1, Powder 1 (10) exhibits crystalline peaks (50).

To prepare Powder 2, approximately 30 grams of a barium borosilicate glass filler having an average particle size of 0.4 micrometer (Schott 8235) was added to 402 grams of a zirconium acetate solution (containing about 15 percent zirconium) (NYACOL®ZRO$_2$, Nano Technologies, Inc. The mixture was sonified to break any agglomerated particles. Approximately 900 grams of the Nissan Snowtex PS-M™ sol was slowly added into the above mixture over about 30 minutes. The pH was about 3.5. The solution was poured into glass trays and the gel-like slurry was dried at approximately 70° C. overnight. The dried powder was collected and pulverized to break any agglomerates. The powder was sintered at about 950° C. for about one hour. The sintered powder was then ground and subjected to an x-ray diffraction measurement. The bottom curve in FIG. 1 shows that Powder 2 (20) has many crystalline peaks (50).

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A polycarbonate-modified diphenoxy diacrylate resin composition having a monomer formula:

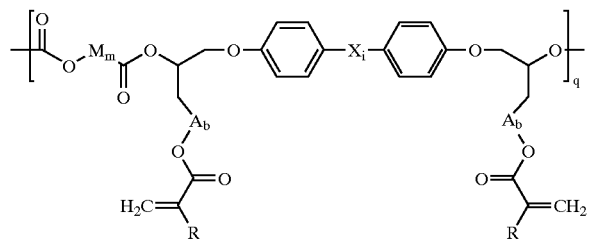

wherein R is $CH_3$ or H; b is one or zero; A is $O(CH_2)_n$; n is an integer from 1 to 0; X is an alkyl or cycloalkyl group having from one to six carbons, S, or O; i is 1 or 0; M is an alkyl or cycloalkyl group having from one ten carbon atoms; m is an integer from one to ten; and q is an integer from 1 to about 100.

2. The resin composition of claim 1, wherein R, is $CH_3$, b is zero, i is one, X is —$CH_2$— or 2,2-propylene, M is —$(CH_2)_pO$— wherein p is an integer from one to four or —$CH(CH_3)CH_2O$—, and m is 1, 2, or 3.

3. The resin composition of claim 2, wherein X is —$CH_2$—.

4. The resin composition of claim 3, wherein m is 2 or 3.

5. The rein composition of claim 4, wherein M is —$CH_2CH_2O$—.

6. The resin composition of claim 2, wherein X is 2,2-propylene.

7. The resin composition of claim 6, wherein m is 2 or 3.

8. The resin composition of claim 7, wherein M is —$CH_2CH_2O$—.

9. The resin composition of claim 1, wherein A is —$CH_2CH_2O$—, X is —$CH_2$—, i is 1, and b is 1.

10. The resin composition of claim 9, wherein m is 1, 2 or 3.

11. The resin composition of claim 10, wherein M is —$CH_2CH_2O$—.

12. The resin composition of claim 1, further comprising an additional ethylenically unsaturated resinous monomer or oligomer in an amount of about 20 to about 90 percent by weight of the total resin composition.

13. The resin composition of claim 12, wherein the additional ethylenically unsaturated resinous monomer or oligomer is a polyurethane dimethacrylate, urethane dimethacrylate, diurethane dimethacrylate, or a combination thereof.

14. The resin composition of claim 1, further comprising from about 0 to about 40 weight percent of a diluent monomer based on the total composition.

15. The resin composition of claim 14, wherein the diluent monomer is 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, 1,6-hexanedioldimethacrylate, or a combination thereof.

16. The resin composition of claim 1, further comprising at least one inorganic filler.

17. The resin composition of claim 16, wherein the inorganic filler is a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, or a combination thereof.

18. The resin composition of claim 1, further comprising a filler material comprising silica particles derived from a nanoparticulate silica sol, the filler having at least one crystalline phase.

19. The resin composition of claim 18, wherein the filler material further comprises a glass filler, a ceramic filler, or a mixture thereof; and further wherein the glass filler, ceramic filler, or mixture thereof comprises microparticulates.

20. A dental restoration comprising the resin composition of claim 1.

* * * * *